United States Patent
Pohlad et al.

(10) Patent No.: US 9,693,948 B1
(45) Date of Patent: Jul. 4, 2017

(54) APPLE CIDER VINEGAR RINSE

(71) Applicants: Donna Pohlad, Minneapolis, MN (US); Virginia Gregg, Inver Grove Heights, MN (US)

(72) Inventors: Donna Pohlad, Minneapolis, MN (US); Virginia Gregg, Inver Grove Heights, MN (US)

( * ) Notice: Subject to any disclaimer, the term of this patent is extended or adjusted under 35 U.S.C. 154(b) by 0 days.

(21) Appl. No.: 15/291,436

(22) Filed: Oct. 12, 2016

Related U.S. Application Data

(60) Provisional application No. 62/240,844, filed on Oct. 13, 2015.

(51) Int. Cl.
| | |
|---|---|
| *A61K 8/97* | (2017.01) |
| *A61K 8/58* | (2006.01) |
| *A61K 8/84* | (2006.01) |
| *A61K 8/92* | (2006.01) |
| *A61Q 5/12* | (2006.01) |
| *A61Q 5/00* | (2006.01) |

(52) U.S. Cl.
CPC ............. *A61K 8/97* (2013.01); *A61K 8/585* (2013.01); *A61K 8/84* (2013.01); *A61K 8/922* (2013.01); *A61Q 5/00* (2013.01); *A61Q 5/12* (2013.01); *A61K 2800/524* (2013.01)

(58) Field of Classification Search
None
See application file for complete search history.

(56) References Cited

U.S. PATENT DOCUMENTS

| | | |
|---|---|---|
| 4,906,461 A | 3/1990 | Chambers |
| 5,560,916 A | 10/1996 | Koulbanis et al. |
| 5,674,510 A | 10/1997 | Di'Tucci |
| 6,103,272 A | 8/2000 | Keeney |
| 7,655,262 B2 | 2/2010 | Chambers |
| 9,198,852 B2 | 12/2015 | Burt et al. |
| 2005/0002884 A1 | 1/2005 | Jefferson |
| 2006/0286062 A1 | 12/2006 | Schep et al. |

FOREIGN PATENT DOCUMENTS

| | | | |
|---|---|---|---|
| CN | 105456071 | 4/2016 | |
| FR | 2510402 | 2/1983 | |
| WO | 2009059814 | 5/2009 | |
| WO | WO 2011081907 A1 * | 7/2011 | ............ A61K 8/737 |
| WO | 2015148523 | 10/2015 | |

OTHER PUBLICATIONS

Coconuts and Kettlebells, Apple Cider Vinegar Hair Rinse, http://coconutsandkettlebells.com/apple-cider-vinegar-hair-rinse/, Nov. 4, 2016, pp. 1-59.

Chagrin Valley Soap and Salve, Make Your Own Natural Vinegar Hair Rinse, http://www.chagrinvalleysoapandsalve.com/idascorner/shampoo-hair/make-your-own-natural-vinegar-hair- . . . , Jul. 29, 2016, pp. 1-7.

Jabs, Homemade Conditioner for Hair, www.diynatural.com/homemade-conditioner, Jul. 29, 2016, pp. 1-31.

Hudson, How to Use Apple Cider Vinegar for Beautiful Hair and Skin, http://www.huffingtonpost.com/organic-authoritycom/apple-cider-vinegar-beauty-b 1924 . . . , Jul. 29, 2016, pp. 1-3.

Evine, dpHUE ACV by dpHUE Apple Cider Vinegar Hair Rinse 8.5 oz—309-911, http://www.evine.com/Product/309-911, Jul. 29, 2016, pp. 1-3.

DpHUE, Apple Cider Vinegar Hair Rinse, http://www.ofakind.com/shop/product/3308-apple-cider-vinegar-hair-rinse, Jul. 29, 2016, pp. 1-4.

\* cited by examiner

*Primary Examiner* — Ernst V Arnold
*Assistant Examiner* — Kyung Sook Chang
(74) *Attorney, Agent, or Firm* — Briggs and Morgan, P.A.; Daniel A. Rosenberg

(57) ABSTRACT

The present invention relates to a hair care product. In particular, the invention relates to an apple cider vinegar hair texturizing rinse product.

23 Claims, No Drawings

APPLE CIDER VINEGAR RINSE

RELATED APPLICATIONS

The present application claims priority to, and incorporates by reference U.S. Provisional Patent Application No. 62/240,844 filed on Oct. 13, 2015.

BACKGROUND

This invention relates to a hair care product. In particular, the invention relates to an apple cider vinegar hair cleansing and conditioning rinse product.

BACKGROUND OF THE INVENTION

Personal care products in general, and hair care products in particular, are a normal part of daily life. Such hair care compositions are useful for nourishment, conditioning, and maintenance of healthy hair and scalp, and are used to improve the physical appearance of the hair. However, many hair care compositions are made from chemicals that can be harmful, or that consumers are unfamiliar with, and that may be damaging to hair or the scalp when used repetitively. There is an increasing interest in hair care products that are made from more natural sources that are effective, environmentally friendly, and familiar to consumers.

Apple Cider Vinegar ("ACV") is a natural product that has been used in various forms and in a wider variety of personal care products for some time. These products include hair care products. Unfortunately, the prior art uses of ACV for hair care in many circumstances have been hampered by the fact that ACV can have harsh and damaging effects on hair, and it has proven very difficult to use ACV in an amount that is effective without damaging the hair or scalp.

What is needed, therefore, is a personal care product, and more specifically a hair care product, that takes advantage of the cleansing elements of ACV but substantially eliminates the other harmful attributes of ACV on hair.

DETAILED DESCRIPTION OF THE PREFERRED EMBODIMENTS

The present invention comprises a hair care product, namely, an ACV-based hair cleanser, rinse, and conditioner. ACV is a natural product made from fermenting apple juice. Bacteria and yeast are used to start the alcoholic fermentation process, and the sugars are turned into alcohol. A secondary fermentation step converts the alcohol into vinegar through the use of acetic acid-forming bacteria.

ACV includes minerals, amino acids, and fatty acids that remove build-up in the hair without the use of harsh surfactants, restoring the natural pH of hair and sealing the cuticle for surprisingly shiny hair. In addition to ACV, the present invention comprises argon oil, fire tulip, lavender extract, aloe vera and other ingredients described in detail below.

Heretofore, the use of ACV has been hampered because ACV has the negative side effect of washing the color out of treated/colored hair. As a result, to avoid a loss of color, prior art products either use less ACV (resulting in less than maximum benefit), or use higher levels of ACV and risk the negative side effects. The product of the present invention overcomes this problem by using color-locking technology and conditioning agents that increase the shine, vibrancy, and softness of hair without loss of color. In fact, the combination of ingredients in the product can enhance hair color by making the hair shinier and less dull. As a result, this combination of ingredients actually permits the use of ACV in concentrations higher than can be found in the prior art, which allows the product to provide greater benefits from the ACV while avoiding the problems traditionally associated therewith, such as loss of color. The product also includes proteins that can triple the strength of hair and protect from heat styling damage and breakage. The product also reduces fizz, and makes hair more manageable.

It is believed that ACV has a synergistic effect whereby it enhances the effect of the other active conditioning ingredients in the product because the ACV removes build up and closes hair cuticles, which allows those products to work better than they would by themselves. Also, the product similarly produces an anti-microbial benefit by cleansing the scalp and hair, removing, and/or preventing bacteria and microbe formation—this benefit results in a reduction in dry and itchy scalp associated with other products or the absence thereof. Also as a result, the combination of VibraRiche and Arlasilk with ACV increased softness in a synergistic manner substantially over combinations that did not include Arlasilk.

To use the product, the scalp and hair should preferably be wet, but with excess water removed. A sufficient amount of product to reasonably coat the hair is applied to the hair (amount will vary based on the amount and type of hair). The product should be left in the hair for about 1 to 3 minutes, and then rinsed out.

The product can be prepared and/or mixed in a conventional manner, complete mixing is preferable. In particular, the product should be thoroughly mixed before the Arlasilk is added. Further, the Arlasilk needs to be less than year and most preferably less than 6 months old, or the product may separate. Once properly mixed the product is stable, and has a reasonable shelf life thereafter.

The product surprisingly provides the following advantages and features, by enhancing the following: color protection, cleansing, wet comb, dry comb, softness, shine, manageability, semi-permanent conditioning, restores pH of scalp and hair, removes product build-up, detangling, restores damaged hair, anti-static, strengthens hair/anti-breakage, and moisturizes.

An embodiment of the product is comprised of the following ingredients, which provide the advantages described therewith and herein (although not wishing to be bound to any particular theory of operation):

| Material | Percent Material | INCI Name | Percent INCI | Functions (per CTFA Dictionary) |
|---|---|---|---|---|
| Purified Water | 71.7498 | Water | 71.7498 | Solvent |
| Styleze W-17 | 2.5 | Polyquaternium-55 | 0.425 | Hair Fixative |
| | | Water | 2.075 | Solvent |

| Material | Percent Material | INCI Name | Percent INCI | Functions (per CTFA Dictionary) |
| --- | --- | --- | --- | --- |
| VibraRiche | 2.2 | Rapeseedamidopropyl Ethyldimonium Ethosulfate | 1.1 | Anti-Static Agent |
|  |  | Quaternium-96 | 0.44 | Hair Conditioner |
|  |  | Propanediol | 0.22 | Solvent |
|  |  | Dipropylene Glycol | 0.44 | Solvent |
| N-durHance A-1000 | 5 | Polyacrylamidopropyltrimonium Chloride | 1 | Hair Conditioner |
|  |  | Water | 4 | Solvent |
| Incroquat CTC-30 | 5 | Cetrimonium Chloride | 1.5 | Anti-Static Agent, Hair Conditioner, Biocide, Emulsifier |
|  |  | Water | 3.5 | Solvent |
| Silsense Q-Plus | 1.5 | Silicone Quaternium-8 | 1.5 | Hair Conditioner |
| Apple Cider Vinegar | 7 | Apple Cider Vinegar | 7 | Hair Conditioner, pH Ajduster |
| Arlasilk PLN | 2 | Linoleamidopropyl PG-Dimonium Chloride Phosphate Dimethicor | 0.5 | Hair Conditioner |
|  |  | Water | 1.5 | Solvent |
| Glycerin 99.5%, USP | 1 | Glycerin | 1 | Humectant, Skin Conditioner |
| Dissolvine GL-47-S | 0.15 | Tetrasodium Glutamate Diacetate | 0.0705 | Chelator (used to enhance preservative efficacy) |
|  |  | Water | 0.0795 | Solvent |
| RITALOE 1X | 0.1 | *Aloe Barbadensis* Leaf Juice | 0.001 | Humectant, Skin Conditioner |
|  |  | Water | 0.099 | Solvent |
| Argan Oil | 0.0001 | *Argania Spinosa* Kernel Oil | 0.0001 | Hair Conditioner |
| Macadamia Oil | 0.0001 | *Macadamia Ternifolia* Seed Oil | 0.0001 | Hair Conditioner |
| Keravis | 1 | Hydrolyzed Vegetable Protein PG-Propyl Silanetriol | 0.25 | Hair Conditioner |
|  |  | Water | 0.75 | Solvent |
| Phytofleur Fire Tulip | 0.1 | *Spathodea Campanulata* Flower Extract | 0.005 | Skin Conditioner |
|  |  | Glycerin | 0.025 | Humectant, Skin Conditioner |
|  |  | Water | 0.07 | Solvent |
| ABS Dandelion Extract | 0.1 | *Taraxacum Officinale* (Dandelion) Leaf Extract | 0.02 | Skin Conditioner |
|  |  | Water | 0.08 | Solvent |
| ABS Lavender Extract G PF | 0.1 | *Lavandula Angustifolia* (Lavender) Extract | 0.02 | Skin Conditioner |
|  |  | Glycerin | 0.08 | Humectant, Skin Conditioner |
| Liquid Germall Plus | 0.5 | Diazolidinyl Urea | 0.198 | Preservative |
|  |  | Iodopropynyl Butylcarbamate | 0.002 | Preservative |
|  |  | Propylene Glycol | 0.3 | Humectant, Skin Conditioner |

Additional information about ranges and ingredients is provided below.

Ingredient Ranges: Ranges are of the Raw Material, not the "active" portions (in blank) of the materials.

| Material | Percent Material | Broad Range | Ideal Range | INCI Name | Percent INCI |
| --- | --- | --- | --- | --- | --- |
| Purified Water | 71.7498 | N/A | N/A | Water | 71.7498 |
| Styleze W-17 | 2.5 | 0.5-12 | 1.25-3 | Polyquaternium-55 | 0.425 |
|  |  |  |  | Water | 2.075 |
| VibraRiche | 2.2 | 0.5-10 | 1.5-5 | Rapeseedamidopropyl Ethyldimonium Ethosulfate | 1.1 |
|  |  |  |  | Quaternium-96 | 0.44 |
|  |  |  |  | Propanediol | 0.22 |
|  |  |  |  | Dipropylene Glycol | 0.44 |
| N-durHance A-1000 | 5 | 0.5-10 | 1.5-5 | Polyacrylamidopropyltrimonium Chloride | 1 |
|  |  |  |  | Water | 4 |
| Incroquat CTC-30 | 5 | 1-10 | 3-5 | Cetrimonium Chloride | 1.5 |
|  |  |  |  | Water | 3.5 |
| Silsense Q-Plus | 1.5 | 0.5-10 | 1-3 | Silicone Quaternium-8 | 1.5 |
| Apple Cider Vinegar | 7 | 0.1-20 | 5-10 | Apple Cider Vinegar | 7 |
| Arlasilk PLN | 2 | 0.5-10 | 1-5 | Linoleamidopropyl PG-Dimonium Chloride Phosphate Dimethicor | 0.5 |
|  |  |  |  | Water | 1.5 |
| Glycerin 99.5%, USP | 1 | 0.5-10 | 1-3 | Glycerin | 1 |
| Dissolvine GL-47-S | 0.15 | 0.05-0.5 | 0.1-0.2 | Tetrasodium Glutamate Diacetate | 0.0705 |
|  |  |  |  | Water | 0.0795 |
| RITALOE 1X | 0.1 |  |  | *Aloe Barbadensis* Leaf Juice | 0.001 |
|  |  |  |  | Water | 0.099 |
| Argon Oil | 0.0001 |  |  | *Argania Spinosa* Kernel Oil | 0.0001 |
| Macadamia Oil | 0.0001 |  |  | *Macadamia Ternifolia* Seed Oil | 0.0001 |
| Keravis | 1 | 0.5-10 | 1-5 | Hydrolyzed Vegetable Protein PG-Propyl Silanetriol | 0.25 |
|  |  |  |  | Water | 0.75 |
| Phytofleur Fire Tulip | 0.1 |  |  | *Spathodea Campanulata* Flower Extract | 0.005 |
|  |  |  |  | Glycerin | 0.025 |
|  |  |  |  | Water | 0.07 |

-continued

| Material | Percent Material | Broad Range | Ideal Range | INCI Name | Percent INCI |
|---|---|---|---|---|---|
| Ingredient Ranges: Ranges are of the Raw Material, not the "active" portions (in blank) of the materials. | | | | | |
| ABS Dandelion Extract | 0.1 | | | *Taraxacum Officinale* (Dandelion) Leaf Extract | 0.02 |
| | | | | Water | 0.08 |
| ABS Lavender Extract G PF | 0.1 | | | *Lavandula Angustifolia* (Lavender) Extract | 0.02 |
| | | | | Glycerin | 0.08 |
| Liquid German Plus | 0.5 | 0.1-0.5 | 0.3-0.5 | Diazolidinyl Urea | 0.198 |
| | | | | Iodopropynyl Butylcarbamate | 0.002 |
| | | | | Propylene Glycol | 0.3 |
| TOTALS | 100 | | | | 100 |

The exact ranges can and will vary, based on experimentation, without departing from the scope of the intended invention. In particular, range information is provided below.

The broad pH range is 3-9, preferred range is (3-4), still more preferred is (3.5-4), and most preferred range is (3.7-3.8). The pH range is most effective below 4, but should not be so low that the product becomes harsh.

INCI refers to the International Nomenclature of Cosmetic Ingredients standards.

The functional/active ingredients include the following:

Apple Cider Vinegar. This ingredient is the backbone for the ACV hair rinse product. ACV is diluted with water and used as a hair rinse to provide the advantages set forth herein. ACV is 5% acidity, mainly in the form of acetic acid. But ACV also contains citric, malic, formic, and lactic acids. ACV has the benefit of closing the hair cuticle, and removes oils and dirt by altering the electrical properties of these substances allowing them to better bond to water thereby rinsing out of the hair more effectively, which repairs damage and removes deposits that can results from alkaline hair coloring, perming/straightening, and other aggressive hair treatments, which generally leaves the hair exposed, dry, dull, brittle and frizzy; however, the product of the present invention uses a low pH gentle acid, flattens the cuticle, hardens the outer layer and shrinks the diameter of the hair, thereby making hair smoother and softer. Smoothing the cuticle allows the light to reflect better for shinier looking hair. Cuticle scales that lie more snugly against the hair shaft also prevent moisture loss more efficiently, which helps hair to be stronger and healthier. Additionally, ACV versus distilled vinegar provides nutritional benefits from the fermentation of apple cider, such as vitamins, minerals, amino acids, enzymes, fatty acids and phytosterols. Whereas, distilled vinegar is made by fermentation grain or ethyl alcohol.

Styleze W-17. Styleze W-17 prevents artificial hair color loss from the effects of the ACV. At higher levels, ACV does remove some of the hair color, particularly reds (which are non-oxidative hair dyes). To maintain an effective level of ACV without removing hair color, Styleze W-17 was incorporated into the formula and proved (based on hair test trials) to prevent hair color loss when the ACV rinse was used on freshly colored hair. The level of Styleze was preferably about 2.5%, where color-loss prevention was achieved without noticeable tackiness to the hair—Styleze is a polymer (hair fixative), sticking to the hair and having a tacky feel. Styleze is a commercially available product from Ashland.

N-durHance A-1000. N-durHance provides a semi-permanent conditioning benefit, which enhances the overall benefits of the ACV Rinse. This product is commercially available from Ashland.

Incroquat CTC-30. Incroquat CTC-30 (Cetrimonium Chloride) is an ingredient for conditioners and is particularly used in leave-on detangling, conditioner sprays. It reduces static, conditions, cleanses, and softens the hair. Incroquat is commercially available from Coda, Inc.

VibraRiche Silsense Q-Plus Arlasilk PLN. The combination of VibraRiche, Silsense, and Arlasilk was discovered to provide additional and intense softness and shine. Many different ingredients and ingredient combinations were tried and this combination was found to be superior in the trials. Additionally, all these ingredients (including N-durHance and Cetrimonium Chloride) were selected for their benefits and do not have heavy conditioning agents that build-up and weigh hair down. Arlasilk was found to be important in softness based on use trials with and without Arlasilk. VibraRiche also enriches hair color. Arlasilk and VibraRiche are commercially available from Croda, Inc. Silsense is commercially available from Lubrizol.

Keravis. Keravis is a hair strengthener and is included (at an effective level) as an added benefit to the product. The product is commercially available from Croda, Inc.

Glycerin. Glycerin is used in as a humectant to draw and hold moisture to the hair.

Further discussion of the product benefits is as follows.

The foregoing ingredients are generally available substances commercially available as indicated.

Apple Cider Vinegar

Contains vitamins, minerals, amino acids, enzymes, fatty acids and phytosterols

Removes product build-up for gentle cleansing without harsh surfactants

Restores pH of scalp and hair from coloring/bleaching and use of daily hair products such as shampoos, conditioners and styling products Closes the cuticle for natural detangling and noticeably shiny hair without weighing down the hair like heavy conditioners Revitalizes the hair making it soft and smooth Styleze W—ColorTrue Technology
Polyquaternium-55
 Provides protection of oxidative hair color fading from shampoo washing
 Forms substantive and hydrophobic barrier that seals or reduces sizes of pores and protects layers of cuticle end VibraRiche
Rapeseedamidopropyl Ethyldimonium Ethosulfate, Quaternium-96, Dipropylene glycol, Propanediol
 Enriches hair color by increasing the shine, vibrancy, softness, and condition of the hair
 Promotes longer lasting hair color
 Patented Technology
 Vegetable derived from renewable resources NDurHance A-1000
Polyacrylamidopropyltrimonium Chloride
 Outstanding durable repair and conditioning
 Semi-permanent conditioning effect throughout multiple washes
 Restores damaged hair to the hydrophobic properties of virgin hair, then continues to protect the hair shaft from shampooing, treatments and heat styling
 Significantly improves wet comb-through
 No build-up Silsense Q-Plus
Silicone Quaternium-8
 Superior softening, conditioning, shine and anti-static
 Clean, non-greasy, weightless conditioning
 Improves wet and dry comb properties
 Reduces dry time to minimize thermal and mechanical force damage caused by blow drying and styling Keravis
Hydrolyzed Vegetable Protein PG-Propyl Silanetriol
 Multifaceted protein based complex which acts on all three fundamental parameters of hair strength: tensile properties, bending modulus, and cuticle abrasion
 Penetrates into the hair cortex, building strength from within while providing film forming effects to reinforce, lubricate and protect the surface of the hair
 Triples the strength of damaged hair
 Superior to D-Panthenol in strengthening and anti-breakage properties
 Bleached hair treated with a Keravis conditioner is 175% stronger than virgin hair fibers
 Prolongs the fatigue lifetime of the hair fiber by 36%
 Keravis continues to strengthen the hair even in excess humidity
 Keravis gives a clear visually-perceivable improvement in the appearance of the hair after repeated combing: less damaged, more shine, more aligned fibers and less fuzzy ends Cetrimonium Chloride
 A well-known anti-static conditioner that makes hair smoother, softer and easier to manage
 Provides anti-microbial properties for a healthier scalp and eliminating odor
 Cleanses and prevents build-up on the hair Argan Oil
*Argania Spinosa* Kernel Oil, less than effective levels are included in the product
 Often called "liquid gold", argan oil is extracted from the kernels of the Moroccan Argan Tree
 Extremely rich in fatty acids and Vitamin E for softer, silkier and shinier hair
 Helps to treat split ends, tame frizzy hair, prevent breakage, and decrease shedding
 Also used in styling products to make hair more manageable and adds healthy shine
 Moisturizes, soothes, nourishes and protects the scalp from dry skin issues and chemical/environmental irritation Phytofleur Fire Tulip
*Spathodea Campanulata* Flower Extract, less than effective levels are included in the product
 Rich in flavonoids, anthocyanins, and triterpenoids that are well-known for antioxidant, astringent and soothing properties
 The African Tulip will sooth the scalp caused from irritations, abrasions and infections, resulting in healthier, more lustrous hair Dandelion Extract
*Taraxacum Officinale* (Dandelion) Extract, less than effective levels are included in the product
 Loaded with minerals and vitamins that help balance sebum and treat dry hair issues
 Dandelion infusions add sheen and body Lavender Extract
*Lavandula Angustifolia* (Lavender) Extract, less than effective levels are included in the product
 Calms the scalp and provides anti-septic properties that helps against hair loss and shedding
 Balances oil production making it a great hair care herb for all hair types Aloe Vera
*Aloe Barbadensis* Leaf Juice, less than effective levels are included in the product
 Creates manageable, smooth, silky, shiny, and healthy hair All ingredients levels are shown as percent by weight, unless otherwise specified. Embodiments of the present invention may include other ingredients. Other embodiments of the present invention may not include all the ingredients listed above. Also, ingredients what similar properties may be substituted for any of the ingredients listed above.

Furthermore, alternative to the preferred ingredients can be made while still resulting in an effective, but less preferred product, they are as follows:

Apple Cider Vinegar—Broader Category: Organic Acid can be substituted with any compound/ingredient/ingredient mixture that may function as a pH adjuster (acids, bases or buffering agents), such as, but not limited to: organic acids and salts (including carboxylic acids and salts), and inorganic acids and salts.

Styleze (all forms of, e.g. W-10, W-17, W-20)—Broader Category: Polymeric Quaternary Ammonium Compound can be substituted with any compound/ingredient/ingredient mixture that may protect, preserve, enhance, or brighten hair color, such as, but not limited to: quaternary ammonium compounds, polymers, silicones, amino acids, amides, amines, proteins, betaines, and surfactants.

Arlasilk PLN—Broader Category: Quaternary Ammonium Silicone Compound can be substituted with any compound/ingredient/ingredient mixture that may function as a hair conditioning agent and/or antistatic agent, such as, but not limited to: specifically amodimethicone, and generally quaternary ammonium compounds, polymers, silicones, amino acids, amides, amines, proteins, betaines, and surfactants.

VibraRiche—Broader Category: Quaternary Ammonium Compound can be substituted with any compound/ingredient/ingredient mixture that may function as a hair conditioning agent and/or antistatic agent, such as, but not limited to: quaternary ammonium compounds, polymers, silicones, amino acids, amides, amines, proteins, betaines, and surfactants.

Cetrimonium Chloride—Broader Category: Quaternary Ammonium Compound can be substituted with any compound/ingredient/ingredient mixture that may function as a hair conditioning agent and/or antistatic agent, such as, but not limited to: quaternary ammonium compounds, polymers, silicones, amino acids, amides, amines, proteins, betaines, and surfactants.

N-DurHance A-1000—Broader Category: Polymeric Quaternary Ammonium Compound can be substituted with any compound/ingredient/ingredient mixture that may function as a hair conditioning agent and/or antistatic agent, such as, but not limited to: quaternary ammonium compounds, polymers, silicones, amino acids, amides, amines, proteins, betaines, and surfactants.

Silsense Q-Plus—Broader Category: Quaternary Ammonium Silicone Compound can be substituted with any compound/ingredient/ingredient mixture that may function as a hair conditioning agent and/or antistatic agent, such as, but not limited to: quaternary ammonium compounds, polymers, silicones, amino acids, amides, amines, proteins, betaines, and surfactants.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods, and materials are described below. All publications, patent applications, patents, and other references mentioned herein are incorporated by reference in their entirety to the extent allowed by applicable law and regulations. In case of conflict, the present specification, including definitions, will control.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention. Those of ordinary skill in the art that have the disclosure before them will be able to make modifications and variations therein without departing from the scope of the invention.

The invention claimed is:

1. A hair car composition, comprising:
an apple cider vinegar component where the component comprises about 5-10% of the composition by weight;
a hair color fixative component comprised of polyquaternium-55 where the component comprises about 1.25-3% of the composition by weight;
a hair conditioning component comprised of rapeseedamidopropyl ethyldimonium ethosulfate quaternium-96 where the component comprises about 1.5-5% by of the composition weight;
a hair conditioner comprised of polyacrylamidopropyltrimonium chloride where the component comprises about 1.5-5% of the composition by weight;
a component comprised of cetrimonium chloride where the component comprises about 1.5-5% of the composition by weight;
a hair conditioning component comprised of linoleamidopropyl PG-dimonium chloride phosphate dimethicone where the component comprises about 1-5% of the composition by weight;
a hair conditioning component comprised of hydrolyzed vegetable protein where the component comprised about 1-5% of the composition by weight; and
a glycerin component where the component comprises about 1-3% of the composition by weight.

2. The composition of claim 1 further comprising a solvent other than water.

3. The composition of claim 1 further comprising argan oil.

4. The composition of claim 1 further comprising macadamia oil.

5. The composition of claim 1 further comprising fire tulip.

6. The composition of claim 1 further comprising dandelion extract.

7. The composition of claim 1 further comprising lavender extract.

8. The composition of claim 1 further comprising a preservative.

9. The composition of claim 1 where the apple cider vinegar has an acidity level of about 5%.

10. The composition of claim 1 where the pH level of the composition is about 3-9.

11. The composition of claim 1 where the pH level of the composition is about 3-4.

12. The composition of claim 1 where the pH level of the composition is about 3.7-3.8.

13. A hair car composition, comprising:
an apple cider vinegar component where the component comprises about 7% of the composition by weight;
a hair color fixative component comprised of polyquaternium-55 where the component comprises about 2.5% of the composition by weight;
a hair conditioning component comprised of rapeseedamidopropyl ethyldimonium ethosulfate quaternium-96 where the component comprises about 2.2% by of the composition weight;
a hair conditioner comprised of polyacrylamidopropyltrimonium chloride where the component comprises about 5% of the composition by weight;
a component comprised of cetrimonium chloride where the component comprises about 5% of the composition by weight;
a hair conditioning component comprised of linoleamidopropyl PG-dimonium chloride phosphate dimethicone where the component comprises about 2% of the composition by weight;
a hair conditioning component comprised of hydrolyzed vegetable protein where the component comprised about 1% of the composition by weight; and
a glycerin component where the component comprises about 1% of the composition by weight.

14. The composition of claim 13 further comprising a solvent other than water.

15. The composition of claim 13 further comprising argan oil.

16. The composition of claim 13 further comprising macadamia oil.

17. The composition of claim 13 further comprising fire tulip.

18. The composition of claim 13 further comprising dandelion extract.

19. The composition of claim 13 further comprising lavender extract.

20. The composition of claim 13 further comprising a preservative.

21. The composition of claim 13 further comprising a solvent other than water, argan oil, macadamia oil, fire tulip, dandelion extract, lavender extract, a preservative.

22. The composition of claim 1 further comprising a hair conditioning component comprised of silicone quaternium-8 where the component comprises about 1-3% of the composition by weight.

23. The composition of claim 13 further comprising a hair conditioning component comprised of silicone quaternium-8 where the component comprises about 1.5% of the composition by weight.

* * * * *